United States Patent [19]
Newhouse et al.

[11] 3,982,426
[45] Sept. 28, 1976

[54] RANDOM SIGNAL FLAW DETECTOR SYSTEM

[75] Inventors: Vernon L. Newhouse; George R. Cooper, both of West Lafayette, Ind.

[73] Assignee: Purdue Research Foundation, West Lafayette, Ind.

[22] Filed: Jan. 2, 1975

[21] Appl. No.: 538,190

[52] U.S. Cl. ................................................ 73/67.9
[51] Int. Cl.[2] ........................................ G01N 29/04
[58] Field of Search ............ 73/67.5 R, 67.7, 67.8 R, 73/67.9

[56] References Cited
UNITED STATES PATENTS

| | | | |
|---|---|---|---|
| 2,434,255 | 1/1948 | Bond et al. | 333/30 R |
| 3,228,232 | 1/1966 | Proctor | 73/67.7 |
| 3,295,362 | 1/1967 | Wood et al. | 73/67.9 |
| 3,683,680 | 8/1972 | Johnson et al. | 73/67.7 |
| 3,739,628 | 6/1973 | Saglio | 73/67.7 |

*Primary Examiner*—James J. Gill
*Attorney, Agent, or Firm*—John R. Nesbitt

[57] ABSTRACT

A random signal flaw detection system is disclosed that provides enhanced system sensitivity and/or increased range capabilities as well as being capable of improved resolution where necessary or desired. The system includes a generator which produces random electrical signals which are converted at a transducer into ultrasound for transmission into a test object. The reflected signal is received at a transducer and converted to an electrical signal which is then correlated with a delayed sample of the transmitted signal with the output being indicative of the sensed flaws in the test object.

11 Claims, 8 Drawing Figures

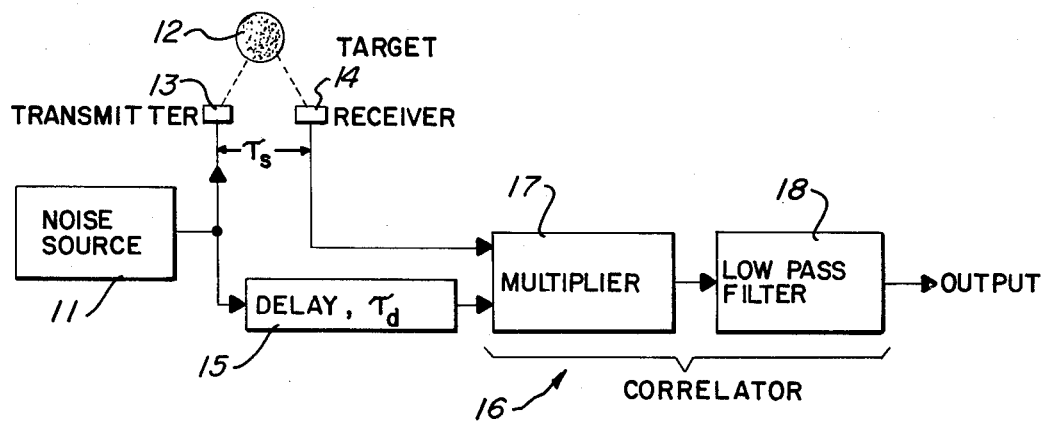
Fig_1
BASIC RANDOM SIGNAL SYSTEM
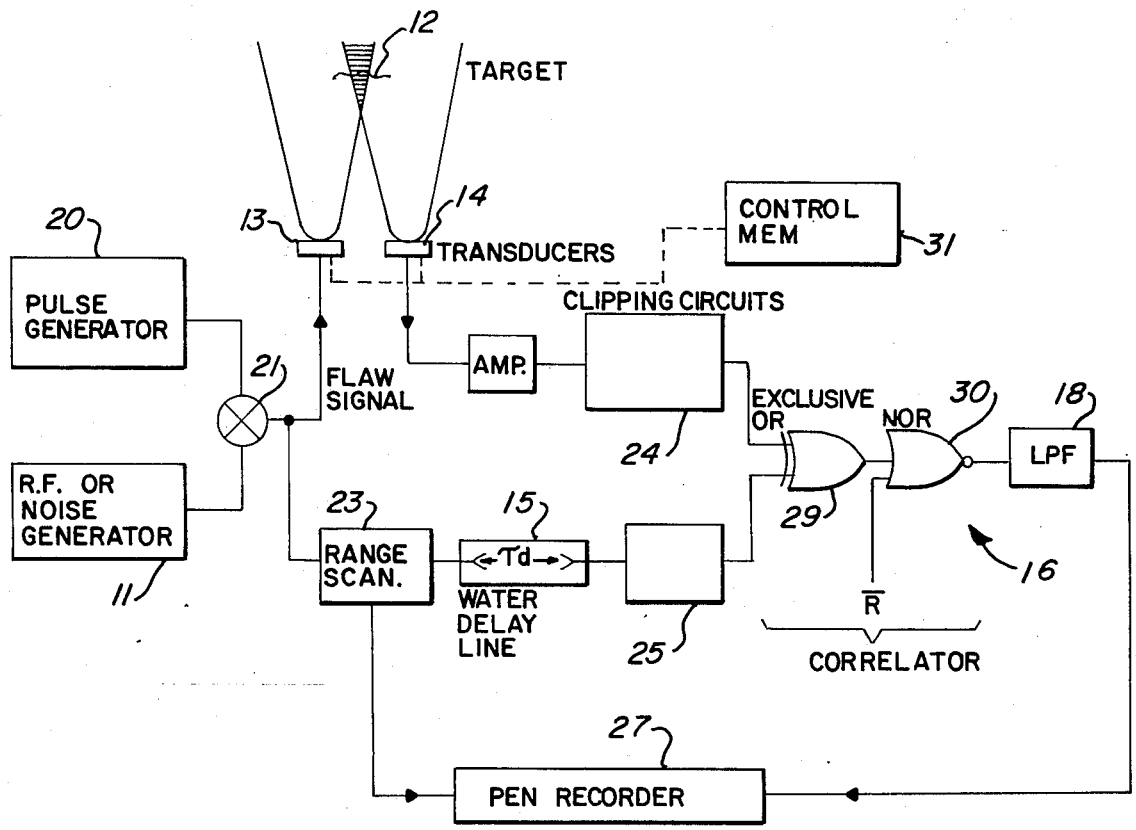
Fig_2

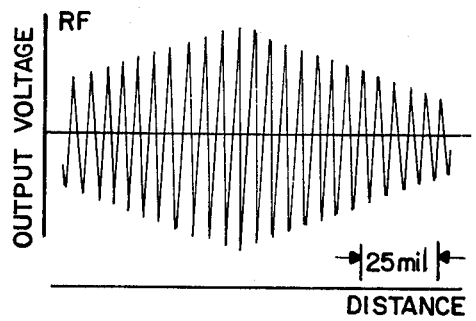
Fig_3
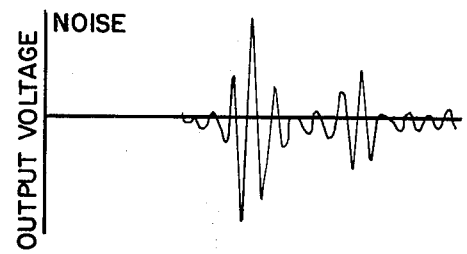
Fig_4
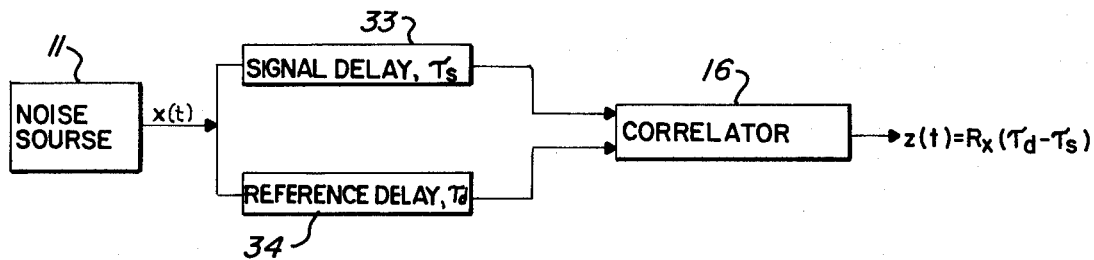
Fig_5
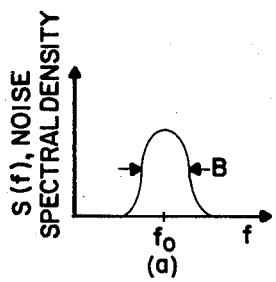
Fig_6
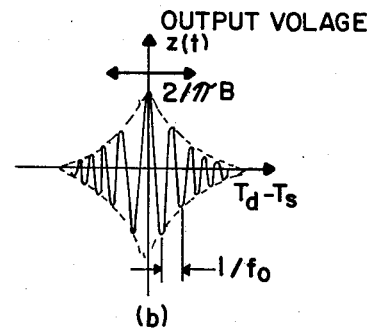
Fig_7
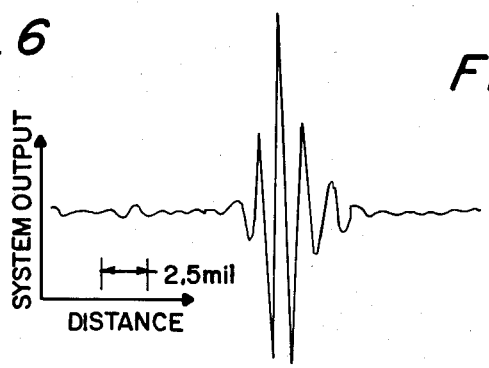
Fig_8

RANDOM SIGNAL FLAW DETECTOR SYSTEM

FIELD OF THE INVENTION

This invention relates to a flaw detection system and more particularly to a random signal flaw detection system.

BACKGROUND OF THE INVENTION

Conventional ultrasonic flaw detectors are presently used to detect flaws produced during the manufacture or use of many types of metals and ceramic components, including, for example, testing of structural members of vehicles for cracks and testing of newly manufactured objects such as ingots and welded steel components for inhomogeneities. The oldest and most widely used ultrasonic flaw detection technique is a pulsed echo type wherein short waves of radio frequency ultrasound are transmitted into a test object with the echoes from inhomogeneities in the object being displayed oscillographically. The time of occurrence and amplitude of these echoes can be related respectively to the location and magnitude of the sound reflected.

Such pulse echo flaw detectors have also been used heretofore, for example, for scanning and imaging organs in the body, particularly the brain. Such scanners have a number of advantages over the other types of scanners utilizing, for example, X-rays, including decreased danger relative to X-ray exposure, but heretofore such scanners have not been capable of the resolution afforded by X-ray systems. However, prior ultrasound systems have not been capable of minimizing exposure danger to the extent desired since sufficiently small intensities have not heretofore been possible while achieving the desired end. In addition, resolution and reverberation problems have been encountered.

The limitations of pulse echo flaw detectors arise from the fact that it is necessary to wait until the most distant echo has returned before transmitting another pulse in order to avoid problems of range ambiguity. Furthermore, to obtain fine range resolutions it is necessary to transmit a correspondingly narrow burst of r.f. energy. The relative parameter may be described as follows:

$$\frac{\text{Maximum Range}}{\text{Range Resolution}} = \frac{\text{Burst Interval}}{\text{Burst Width}} = \frac{\text{Peak Power}}{\text{Average Power}} \quad (1)$$

Thus for pulse echo systems, the ratio of peak-to-average transmitted power has to be at least as large as the ratio of the maximum to the desired range resolution. This ratio will usually be on the order of $10^2$ or more in practical systems. Since transducers are limited in the peak power they can handle by electrical breakdown effects, the large peak to average power ratio required can limit the maximum ratio of range to resolution that can be obtained by pulse echo systems.

The other major problem faced by pulse echo flaw detectors is the fact that strongly sound absorbing material makes it necessary to use the largest possible average transmitted power if the returning echoes are to be larger than the thermal receiver noise. Since ultrasound transducers are strongly limited in average power handling capability by overheating, this limits the range of pulse echo systems when used in strongly sound absorbing or scattering materials.

Since the thermal noise power of amplifiers is proportional to bandwidth, it can be shown that the ratio of the signal-to-noise power at the output of a flaw detection system to that of the output of the echo receiving amplifier is given by the expression $$\frac{SNR_{out}}{SNR_{in}} \alpha \; m \; \frac{B_{in}}{B_{out}} \quad (2)$$

wherein $B_{in}$ and $B_{out}$ are respectively the bandwidths of the input and output of the system and $m$ is the mark-time ratio.

In pulse echo systems currently in use, the bandwidth of the signal received at the receiver and the bandwidth of the output signal emerging from the detector are approximately the same, thus these systems are not able to improve the signal-to-noise ratio of the received echo, and the received echo must therefore be much larger than the thermal noise of the echo of the amplifier.

Time averaging techniques have heretofore been utilized to improve the input signal to noise ratio of flaw detection systems by integrating the echo signals over relatively long time periods. This, however, effectively restricts the output bandwidth.

In at least one known time integration system, a lock-in amplifier is utilized whereas in another known system the echo signal is digitized and a digital computer is then utilized. Both of these prior art systems, however, require transmission of short bursts of r.f. energy and therefore require high peak-to-average power ratios.

Thus, while the flaw detection systems have heretofore been suggested and/or utilized, these systems have not provided completely satisfactory flaw detection and more particularly have not proved to be entirely suitable in providing a system having excellent sensitivity and high resolution while minimizing danger of exposure to, or by limiting, needed intensities.

SUMMARY OF THE INVENTION

This invention provides a system that does not require high intensities and thus minimizes exposure, yet has excellent sensitivity and high resolution. The system includes correlation circuitry and can provide appreciable enhancement in input signals and noise ratio by use of time integration. In addition, the system utilizing noise as a transmitted signal and makes resolution along the ultrasonic beam independent of signal duration. Consequently, the peak-to-average transmitted power can be kept close to unity, so that the maximum power that can be transmitted is not limited by transducer electrical breakdown effects.

It is therefore an object of this invention to provide an improved flaw detection system.

It is another object of this invention to provide a novel random signal flaw detection system.

It is yet another object of this invention to provide a random signal flaw detection system that does not require high intensities and thus minimizes exposure yet has excellent sensitivity and high resolution.

It is still another object of this invention to provide a random signal flaw detection system that includes a correlation receiver and produces appreciable enhancement in input signals and noise ratio by use of time integration.

It is yet another object of this invention to provide a flaw detection system that utilizes noise as the transmitted signal so as to make resolution along the ultrasound beam independent of signal duration.

It is yet another object of this invention to provide a random signal flaw detection system wherein transmitted power is kept close to unity so that the maximum power that can be transmitted is not limited by transducer electrical breakdown effects.

With these and other objects in view which will become apparent to one skilled in the art as the description proceeds, this invention resides in the novel construction, combination, and arrangement of parts substantially as hereinafter described and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a block diagram of the basic random signal system of this invention;

FIG. 2 is a block diagram of an experimental random signal flaw detection system as shown basically in FIG. 1;

FIG. 3 is a graph illustrating r.f. output of the flaw detection system shown in FIG. 2;

FIG. 4 is a graph illustrating noise as a transmitted signal in connection with the system of FIG. 2;

FIG. 5 is a further block diagram illustrating the basic random signal system;

FIG. 6 is a graph illustrating a system waveform for the spectrum of transmitted noise signal;

FIG. 7 is a graph illustrating a system waveform for the correlator output voltage and has a range cell scanned through a pocket or test object; and FIG. 8 is a representation of detection of 1m Au wire in water at a 15 cm range detected by the system of this invention.

DESCRIPTION OF THE INVENTION

Referring now to the drawings, FIG. 1 illustrates, in block diagram form, the basic random signal generating system of this invention. As shown, a noise, or r.f., source 11 produces electric signals which are converted into ultrasound and transmitted into the test object 12 by an ultrasonic electric transducer 13. Echoes reflected from inhomogeneities are picked up by an identical receiving transducer 14 and are reconverted into electric signals. The transducers may be piezoelectric transducers, but could if desired by magnetostrictive transducers. The received signal is then correlated with a sample of the transmitted signal which has been delayed for a period of time by means of delay line 15.

As shown in FIG. 1 the amplified echo signal, together with the reference signal emerging from delay line 15, are coupled to the correlator 16 which includes multiplier 17 followed by an integrator in the form of low pass filter 18. The output is then taken from low pass filter 18.

In the presence of a test object as indicated in FIG. 1, the system will produce a non-zero output when the delay $\gamma_d$ imposed on the reference signal by the delay line equals the time of flight $\gamma_s$ of the acoustic signal from the transmitting transducer to the target and back to the receiver. Under these circumstances the noise signals entering the two inputs of the correlator are identical, causing it to produce a non-zero output. If, however, $|\gamma_s - \gamma_d| >> 1/\pi B_1$ where B is the bandwidth of the transmitted signal, the signals entering the correlator are uncorrelated, and the time averaged output from the correlator is zero. If the length of delay line is changed slowly with time, $\gamma_d$ varies, so that the systems scan over a line in the test object, producing an output on each occasion that the time varying delay $\gamma_d$ is nearly equal to the time of flight $\gamma_s$ of an ultrasound reflecting flaw.

Referring now to FIG. 2, a working embodiment used experimentally for the random signal generating system of this invention is shown. The noise, r.f., source 11 produces electrical signals which are converted into ultrasound and transmitted into the test object 12 by the piezoelectric transducer 13. As indicated in FIG. 2, a pulse generator 20 can be used, as desired, and combined with the output from noise, or r.f., source 11 at summation circuit 21. Echoes reflected from inhomogeneities are picked up by an identical receiving transducer 14 and are reconverted into electrical signals. The received signal is then correlated with a sample of the transmitted signal which has been delayed by $\gamma_d$, by means of a delay line 15 which receives the transmitted signal through a range scanning circuit 23. The echo signal from transducer 13 is amplified by amplifier 24 and the amplified echo signal and the reference signal emerging from the delay line are passed through Schmitt triggers 24 and 25 respectively, acting as clipping circuits. The term 'clipping' is used herein to refer to the process in which a zero mean analog signal is transformed into a binary signal having the same zero crossings. An analog correlator could be used, if desired, without clipping and would provide an advantage of freedom from interference caused by large disturbing signals.

The clipped echo and reference signals are fed into correlator 16 whose gated output is displayed on one axis of a pen recorder 27. The other axis of the recorder is connected to a micrometer (now shown) in range scanning circuit 23 which controls the distance between the transducers (as might be commonly utilized) in the delay line. Clipping the echo and reference signals allows digital processing of these signals, permitting the correlation function to be performed by EXCLUSIVE-OR gate 29 as shown in FIG. 2. the purpose of the following NOR gate 30 is to insure that only correlator outputs from the desired echoes reach the integrator and that thermal noise generated at other times, as well as signals leaking directly from the transmitter to the receiving transducer, are excluded. This is achieved by allowing the NOR gate to pass signals to low pass filter 18 only during the time that reference signals are emerging from the delay line.

To scan a portion of a specimen, the separation between the transducers of the delay line (which transducers are preferably of the same type as transducers 13 and 14) is varied by means of a micrometer which causes the pen of the recorder to traverse. Whenever the reference delay $\gamma_d$ is approximately equal to the time of flight $\gamma_s$, the correlator produces an output which is displayed by the pen recorder. Typical outputs showing the two surfaces of a 1 mm diameter wire in water are shown in FIGS. 3 and 4. In addition, transducers 13 and 14 are movable relative to one another by means of control means 31 to thus vary the area of a target or targets to be sensed. As will be appreciated, movement of either the transmitter transducer or the receiver transducer relative to the other will vary the overlapping paths between the two and hence determine the portion of the target to be tested for flaws.

Under conditions where the thermal amplifier noise is negligible compared to the echo signal, where no signal clipping is used, and where the correlator is of the analog type, the system can be modeled, as shown in FIG. 5, where both the reference signal delay $\gamma_d$ and the signal time of flight delay $\gamma_s$ are represented by delay lines 33 and 34. The correlator output corresponds to the time average of the product of the two delayed versions of the transmitted noise signal. This time average is the autocorrelation function $R_x(\gamma_s - \gamma_d)$ of the transmitted noise signal $x(t)$.

FIG. 6 shows a typical spectrum of the transmitted noise signal $$S_x(f) = \frac{(B/2)^2}{(B/2)^2 + (f - f_o)^2} \quad (3)$$

where $f_o$ is the center frequency and B is the bandwidth. FIG. 7 shows the output $R_x(\gamma_s - \gamma_d)$ which is the inverse Fourier transform of $S_x(f)$ and may be written as $$R_x(\tau_s - \tau_d) = \frac{B}{2} e^{-\pi B |\tau_d - \tau_s|} \cos 2\pi_o (\tau_d - \tau_s) \quad (4)$$

It can be seen that the time average of the correlator output reaches a maximum when $\gamma_s = \gamma_d$. It is also clear that the correlator output falls to $1/e$ of its maximum when $\gamma_d - \gamma_s$ equals $1/B$. Thus it can be shown that the range resolution of this system is $$\Delta R = \frac{c}{2\pi B} \quad (5)$$

If the bandwidth of the transmitted signal approaches the maximum signal frequency, then it can be shown that the range resolution approaches the theoretical minimum of one-quarter wavelength of the maximum transmitted frequency.

Equation 5 is an extremely important result since it demonstrates that the resolving power of the random signal system depends purely on the bandwidth and not on the time duration of the transmitted signal as in pulse echo systems. Furthermore, since every burst of transmitted noise is different, no range ambiguity results even if additional bursts are transmitted before the last echo of the previous burst has returned to the receiver. A random signal system can thus transmit noise almost continuously so that the ratio of peak-to-average transmitted power approaches unity.

Another important property of the random signal flaw detection system is that its sensitivity can be made almost arbitrarily large by simply increasing the integration time of the correlator.

As shown in Equation 2, the signal-to-noise ratio enhancement is proportioned to the ratio of input to output bandwidth multiplied by the mark-space (on app.) ratio of the transmitted signal. For pulse echo systems this ratio was shown to be unity since input and output bandwidths are comparable. However, this is not the case for the random signal system since the bandwidth at the receiver is determined by the transmitted bandwidth $B_{in}$ while the output bandwidth $B_{out}$ equals the reciprocal of the integration time T of the correlator which can be made arbitrarily long. The signal-to-noise ratio improvement for the experimental system as shown in FIG. 2 follows:

Let the inputs to the clipping circuits in FIG. 2 be defined as $$r(t) = x(t - \gamma_d) \quad (6)$$

and $$y(t) = ax(t - \gamma_s) + n(t) \quad (7)$$

where $r(t)$ and $y(t)$ are the delay side and signal side inputs respectively and $x(t)$ is the transmitted signal which is stationary, zero mean and Gaussian distributed.

In the experimental system analog signals $r(t)$ and $y(t)$ are first clipped and then passed through a polarity coincidence correlator whose output corresponds to the product of the clipped inputs. The mean of this product is a well known result, which can be written as $$E(z(t)) = \frac{2}{\pi} \sin^{-1} \frac{R_{ry}(t)}{\sigma_x \sigma_y} \quad (8)$$

where $\sigma_y^2$ is the variance of the echo amplifier output and is given by $$\sigma_y^2 = a^2 \sigma_x^2 + \sigma_n^2 \quad (9)$$

The signal at the output of the correlator will attain a maximum at $t = 0$, given by $$E_m(z(t)) = \frac{2}{\pi} \sin^{-1} \frac{a \sigma_x}{\sigma_y}$$

$$= \frac{2}{\pi} \frac{a \sigma_x}{\sigma_y} \quad (10)$$

Since the correlator is followed by a low pass filter having a bandwidth of W, the system output noise power will be $$\sigma_o^2 = 2 W S(o) = \frac{2W}{\pi B} \quad (11)$$

where B is the transmitted signal bandwidth. The signal-to-noise power ratio at the input is given by $$(SNR)_i = \frac{a^2 \sigma_x^2}{\sigma_n} \quad (12)$$

Combining Equations 9 – 12 we obtain $$(SNR)_o = (2/\pi) \, BT \, (SNR)_i \quad (13)$$

for $(SNR)_i \ll 1$ where T is the integration time of the filter.

If the transmitted signal, instead of being continuous, has a mark-space ratio, a, then the correlation gain of the clipped random signal flaw detection system becomes $$\frac{(SNR)_o}{(SNR)_i} = \frac{2a}{\pi} BT \qquad (14)$$

where $a$ is the mark-space ratio, B is the bandwidth of a Gaussian noise transmitted, and T is the integration time of the correlator. Since this result was derived for a stationary random transmittal signal, it must also be true for periodic transmitted signals, e.g. short bursts of r.f. as used in conventional pulse echo systems. This correlation gain is seen to be a factor of $2/\pi$ smaller than the value of aBT which is known to hold for both deterministic and random signal analog correlation receivers producing a d.c. signal.

The experimental results described below verify Equation 14 and demonstrate that enhancement ratios of the order of thousands can be obtained.

The system described above has been operated successfully to detect artificial flaws consisting of wires in water, both when transmitting ultrasound in bursts of a 4.8 $MH_2$ sine waves (subsequently referred to as r.f.) or bursts of 2 $MH_2$ bandwidth random signals with a 4.8 $MH_2$ center frequency (subsequently referred to as "noise"). In the experiments described here, the transmitting and receiving transducers of the system were arranged almost parallel so that their beams overlapped as shown in the shaded region in FIG. 2. By moving one of the transducers in the water delay line with a micrometer, the internal delay of the reference signal was changed, thus scanning the system across a series of targets. In these experiments, both the wire targets and the transducers were immersed in a water bath. The outputs of the system were recorded by a pen recorder which produces the type of display shown in FIGS. 3 and 4. Here the X axis corresponds to the spatial coordinate and the Y axis corresponds to the strength of the echo from various targets.

FIGS. 3 and 4 correspond to the observation of a 1 mm copper wire; FIG. 3 shows the output when a 4 usec burst of 4.8 $MH_2$ r.f. is transmitted and FIG. 4 shows the output for 2 $MH_2$ bandwidth noise of the same burst length. Notice that the r.f. signal can detect the presence of the wire but cannot resolve the front and back edges. Inspection of FIGS. 3 and 4 shows that this particular system, using noise, could have resolved targets with a separation as small as 250 microns in water. FIG. 8 shows the correlator output for a 1 mil of Au wire. It is clear from this plot that because of its high sensitivity the system is able to detect targets far smaller than its resolution limit.

It should be noted that that output pattern produced by the system when using noise agrees very closely with that predicted theoretically and illustrated in FIGS. 6 and 7. FIGS. 3 and 4 clearly illustrate that the range resolution of noise is much higher than that of pulsed r.f. of equal duration but lower bandwidth. It should be noted, however, that the improvement of the signal-to-noise ratio produced by our correlation type system is evident not only when transmitting noise but also when transmitting r.f. energy.

The correlation gain of a system using clipped signals, a polarity coincidence correlator, and having input signal-to-noise ratios, much less than unity is given in Equation 14. Four our low-pass filter pen recorder combination with a measured time constant T = 120 msec and transmitted bandwidth of a $MH_2$, this equation predicts a signal-to-noise ratio enhancement of approximately $8 \times 10^3$ with the mark-space ratio of 1/20 that was used. The measured signal-to-noise ratio enhancement agreed with the predicted value to well within the experimental uncertainty.

It is believed that the signal-to-noise enhancement-ratio quoted above could be increased by an order of magnitude simply by increasing the mark-space ratio to one-half from 1/20. This is not experimentally verified since it was already difficult to measure the enhancement ratio of $8 \times 10^3$. Further increase in enhancement would have been extremely difficult to measure and would probably be inaccurate due to leakage effects at high attenuations.

The achieved results show that a simple correlation type ultrasound receiver can detect echoes which have at least 8000 times less power than the thermal receiver noise without any noticeable problems due to mechanical vibration or electronic instabilities. Several further orders of magnitude improvement in sensitivity may be possible be simply lengthening the system integration time above the 0.1 sec. used in this work and using a larger mark-space ratio for the transmitted signal.

Following earlier work originally done for radar, it has been established that when using noise as the transmitted signal, no range ambiguities exist, so that a signal can be transmitted almost continuously. This lessens the peak-to-average transmitted power to near unity, thus lessening the risk of transducer electrical breakdown. It has also been established that the system can easily detect the presence of 25 micron wire targets (or flaws) which are far smaller than the present lower resolution limit of 250 microns.

When operating at high resolution, the system described can trade speed for sensitivity by varying the integration time of the correlator output. When examining objects which are expected to contain a very small number of flaws, increased speed can be obtained without sacrificing sensitivity, by narrowing the transmitted spectrum, thus enlarging the range cell. (The range cell is that region of space from which the scattered signal will correlate with the delayed version of the transmitted signal).

The fact that the system has much greater sensitivity and uses much lower peak-to-average transmitted power than conventional systems enables it to greatly extend the size of strongly absorbing objects that can be examined by ultrasound, or to use higher frequencies which are too strongly absorbed to be practical at present, and thus obtain greatly improved resolution. The ability of a random signal correlation system to provide high sensitivity for a given transmitted power also makes it possible to reduce the peak-to-average power required for a given sensitivity. This feature and the absence of range ambiguity may also make such systems of interest for organ scanning, particularly in the case of the brain, where the skull produces undesirably large absorption and reverberation.

Thus, the system of this invention provides a random signal flaw detector system not heretofore known that has outstanding characteristics in accomplishing the intended purpose.

What is claimed is:

1. A flaw detection system, comprising:
   a random noise source producing an output signal in the ultrasound frequency range;
   a transmitter to transmit said output signal from said random noise source toward a target to be inspected for flaws;

delay means connected with said noise source to receive the output signal coupled to said transmitter;

a receiver to receive said output signal when reflected back from said target under inspection; and correlator means including an exclusive-OR circuit, a NOR gate, and a low pass filter, said exclusive-OR circuit being connected with said delay means and said receiver to receive the outputs therefrom, said correlator means responsive to receipt of outputs by said exclusive-OR circuit from said delay means and said receiver providing an output indicative of predetermined characteristics of a flaw in the target.

2. The flaw detection system of claim 1 wherein said system includes clipping means connected between said correlator means and said delay means and between said correlator means and said receiver.

3. The flaw detection system of claim 1 wherein said delay means includes a pair of relatively movable transducers the positioning of which determines the delay offered by said delay line.

4. The flaw detection system of claim 1 wherein said random noise signal is combined with a pulsed output signal prior to coupling to said transmitter.

5. The flaw detection system of claim 1 wherein said system includes display means receiving the output from said correlator means, and control means for controlling said delay means whereby scanning of a target and display of flaws is effected.

6. The flaw detection system of claim 5 wherein said display means includes a pen recorder.

7. The flaw detection system of claim 6 wherein said display means includes relatively adjustable ultrasound transducers, and wherein said control means includes a micrometer for controlling the relative positioning between said transducers of said delay means.

8. the flaw detection system of claim 1 wherein said system includes positioning means to position said transmitter and receiver relative to one another whereby said system can scan across a series of targets to inspect the same.

9. A flaw detection system, comprising:

a random noise source producing an output signal in the ultrasound frequency range;

a transmitter to transmit said output signal from said random noise source, said transmission being directed from said transmitter in a predetermined transmitting path;

delay means connected with said noise source to receive the output signal coupled to said transmitter, said delay means having relatively adjustable components, the positioning of which determine the delay introduced by said delay means;

a receiver to receive said output signal when reflected back from a target inspected for flaws, said receiver receiving only output signals in a predetermined receiving path of said transmitter at said target area;

correlator means including an exclusive-OR circuit, a NOR gate, and a low pass filter, said exclusive-OR circuit being connected with said delay means and said receiver to receive the outputs therefrom, said correlator means responsive to receipt of outputs by said exclusive-OR circuit from said delay means and said receiver producing an output indicative of a flaw in said intersecting receiving and transmitting paths at said target area; and means to control the relative positioning of said components of said delay means whereby said system can scan across a target range to inspect the target for flaws.

10. The flaw detection system of claim 9 wherein said components of said delay means are relatively movable ultrasound transducers.

11. The flaw detection system of claim 9 wherein said system includes display means for displaying indications of detected flaws in a target, and wherein said means to control the relative positioning of said components of said delay means is also connected with said display means to control the movement of the same in conjunction with positioning of said components of said delay means.

* * * * *